United States Patent [19]

Uosaki et al.

[11] Patent Number: 5,210,893
[45] Date of Patent: May 18, 1993

[54] COUCH APPARATUS FOR MEDICINE

[75] Inventors: Yasuhiro Uosaki; Takuhiro Ōsawa, both of Tochigi, Japan

[73] Assignee: Kabushiki Kaisha Toshiba, Kawasaki, Japan

[21] Appl. No.: 754,624

[22] Filed: Sep. 4, 1991

[30] Foreign Application Priority Data

Sep. 4, 1990 [JP] Japan .................. 2-236832

[51] Int. Cl.⁵ .............. A61G 13/00; A61G 13/02; A61G 13/06
[52] U.S. Cl. .......................... 5/601; 5/600
[58] Field of Search ................ 5/601, 600, 611; 378/209, 208; 108/143

[56] References Cited

U.S. PATENT DOCUMENTS

| | | | |
|---|---|---|---|
| 4,131,802 | 12/1978 | Braden et al. | 5/81.1 |
| 4,475,072 | 10/1984 | Schwehr et al. | 5/601 |
| 4,545,571 | 10/1985 | Chambron | 5/601 |
| 4,615,042 | 9/1986 | Scmmedemann | 5/601 |
| 4,761,000 | 8/1988 | Fischer et al. | 5/601 |
| 4,773,637 | 9/1988 | Jarin | 5/601 |

Primary Examiner—Alexander Grosz
Attorney, Agent, or Firm—Limbach & Limbach

[57] ABSTRACT

A couch apparatus for medical use, comprising a lower base fixed on the floor, an elevating mechanism mounted on the lower base, an upper base fixed on the elevating mechanism, a tabletop mounted slidably on the upper base, and a tabletop slide mechanism. The tabletop is provided with a belt having end portions fixed to end portions of the tabletop along the longitudinal axis of the tabletop. The belt has a slack intermediate portion. The upper base is provided with a drive pulley which engages the intermediate portion of the belt. The upper base is also provided with driving means for rotating the drive pulley and with belt guide rollers for restricting lateral motion of the belt as the drive pulley moves the belt and tabletop longitudinally.

10 Claims, 8 Drawing Sheets

COUCH APPARATUS FOR MEDICINE

BACKGROUND OF THE INVENTION

1. Field of the Invention

The present invention relates to a couch apparatus for medical use, such as use with a magnetic resonance imaging apparatus, an x-ray CT scanner, or [and] a SPECT apparatus.

2. Description of the Related Art

For medical use, this type of couch apparatus is situated near an apparatus for diagnosis or treatment, and is designed to move a desired portion of a subject to the apparatus for diagnosis or treatment. The couch apparatus generally comprises a lower base fixed on the floor, an elevating mechanism mounted on the lower base, an upper base fixed on the elevating mechanism, a tabletop installed slidably on the upper base, and a tabletop sliding mechanism.

Figure 1:
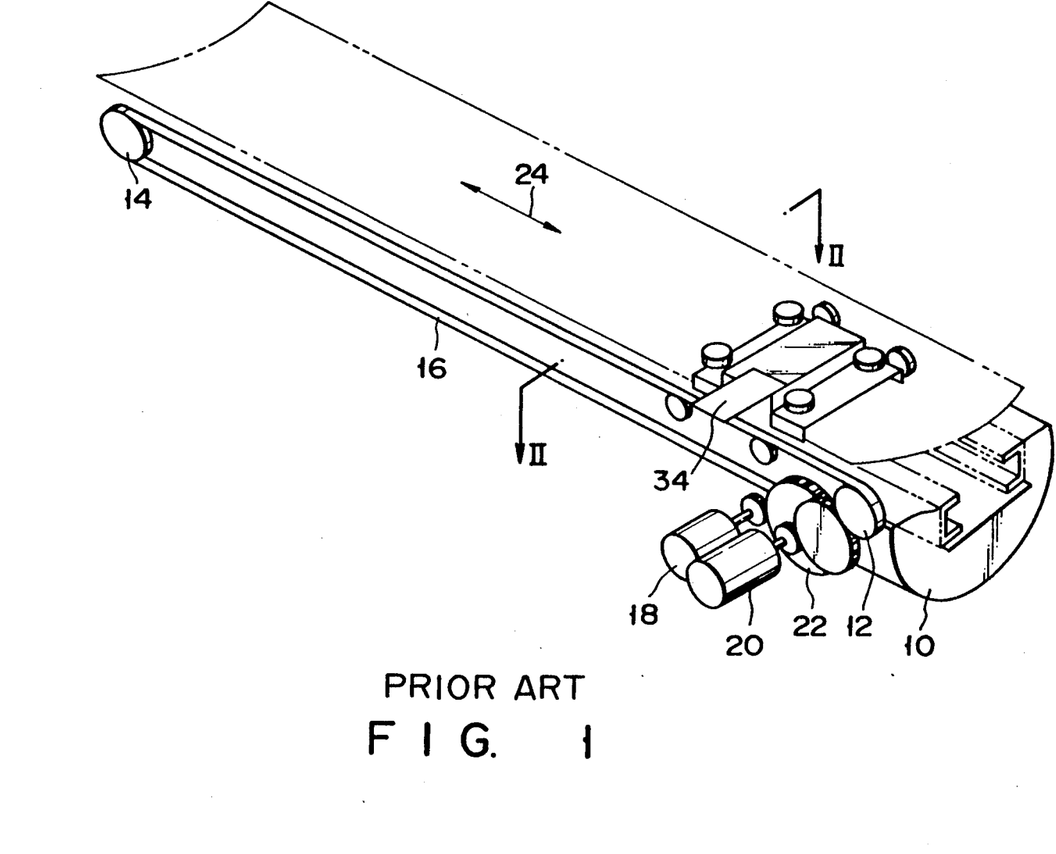
FIG. 1 is a partial perspective view of a conventional couch apparatus, including in particular, an upper base, a tabletop and a tabletop sliding mechanism.

A conventional couch apparatus will now be described with reference to FIG. 1. FIG. 1 is a perspective view of an upper base, a tabletop and a tabletop sliding mechanism of the couch apparatus. As shown in FIG. 1, a first pulley 12 is provided on the side face of one end portion of upper base 10, and a second pulley 14 is provided on the side face of the other end portion of the upper base 10. An endless belt 16 is passed over the first and second pulleys 12 and 14. The upper base 10 is provided with a gear mechanism 22 including an AC motor 18 and a clutch 20. The gear mechanism 22 is driven by the AC motor 18 to run the endless belt 16 in a forward direction and a reverse direction, as indicated by a double-headed arrow 24.

The upper base 10 is provided with a pair of guide rails 26 (shown in FIG. 3), each having a substantially C-shaped cross section. The guide rails 26 extend in the longitudinal direction of the upper base 10. A roller mechanism 28 (shown in FIG. 2) is provided so as to be slidable along the guide rails 26. A table-top 30 (shown in FIG. 2) is situated on the upper base 10, and the roller mechanism 28 is fixed on the lower surface of the tabletop 30. One end of a coupling member 34 is fixed to the roller mechanism 28, and the other end thereof is fixed to the endless belt 16.

Figure 2:
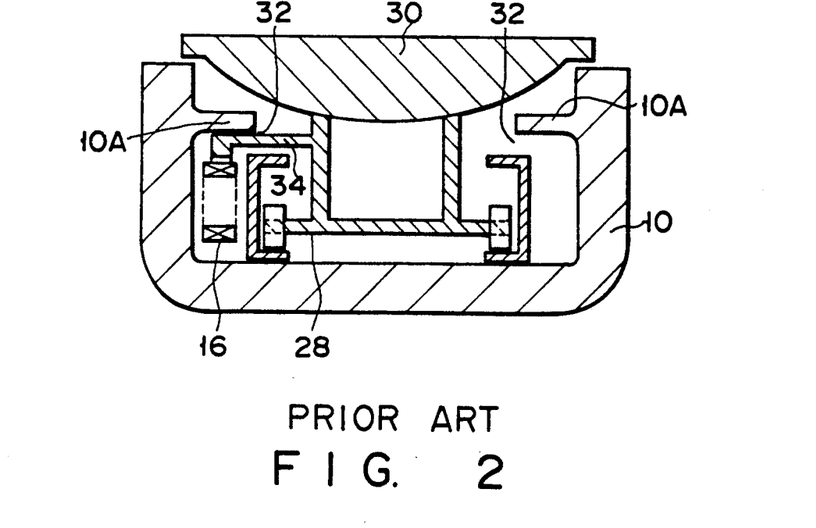
FIG. 2 is a cross-sectional view taken along line II—II in FIG. 1.
Figure 3:
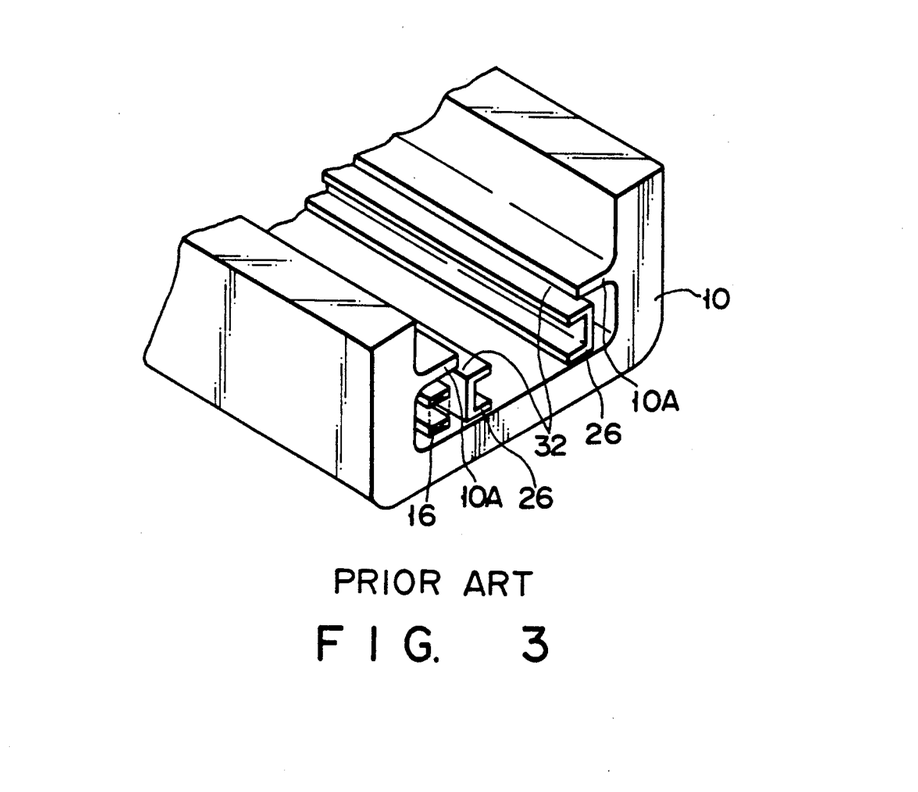
FIG. 3 is a perspective view of a portion of the apparatus shown in FIG. 2.

FIG. 2 is a cross-sectional view taken along line II—II in FIG. 1. Referring to FIG. 2, the structure of the tabletop sliding mechanism including the upper base 10, tabletop 30 and roller mechanism 28 of the couch apparatus will be clearly understood. In FIG. 2, reference numeral 10A denotes flanges formed along the longitudinal axis of the upper base 10. The flanges 10A function to cover the endless belt 16.

In the above structure, the AC motor 18 is driven by a driver and a controller (both not shown) to run the endless belt 16 in the forward and reverse directions indicated by the arrow 24. When the endless belt 16 runs forward, the tabletop 30 approaches an apparatus body (not shown). When the belt 16 runs in a reverse direction, the tabletop 30 moves away from the apparatus body. The direction of movement of the belt 16 is switched by the clutch 20.

The above-described conventional couch apparatus for medicine has the following drawbacks. When the tabletop 30 is moved, such mechanical components as guide rails 26 mounted on the upper base 10, endless belt 16 and pulleys 12 and 14 provided on the side face, and coupling member 34 coupled to the endless belt 16 are exposed to a subject resting on tabletop 30. Thus, the subject may have discomfort. In addition, the exposure of the mechanical components degrades the external appearance of the medical apparatus.

When tabletop 30 moves closest to the apparatus body, the fingers of a subject resting on tabletop 30 may inadvertently be put in gaps 32 between the flanges 10A and the guide rails 26, and the fingers may be fractured.

SUMMARY OF THE INVENTION

The object of the present invention is to provide a couch apparatus for medical use which does not cause discomfort to a subject resting thereon due to the structure of an upper base, has good external appearance as a medical apparatus, and ensures safety for the operator.

This object can be achieved by a couch apparatus having a tabletop on which a subject is placed, and a base structure on which the tabletop is slidably mounted, said couch apparatus comprising:

belt means having end portions fixed to end portions of the tabletop, wherein the belt means has a longitudinal axis and has a slackened intermediate portion between its end portions;

a drive pulley means mounted on the base structure in engagement with said intermediate portion of the belt means; and a driving means mounted on the base structure in engagement with the drive pulley means, for rotating the drive pulley means.

The above object can also be achieved by a couch apparatus having a tabletop on which a subject is placed, and a base structure on which the tabletop is slidably mounted, said couch apparatus comprising:

rack gear means provided along the longitudinal axis of a bottom surface of the tabletop;

pinion gear means mounted on the base structure and meshed with the rack gear means; and drive means mounted on the base structure for rotating the pinion gear means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 4:
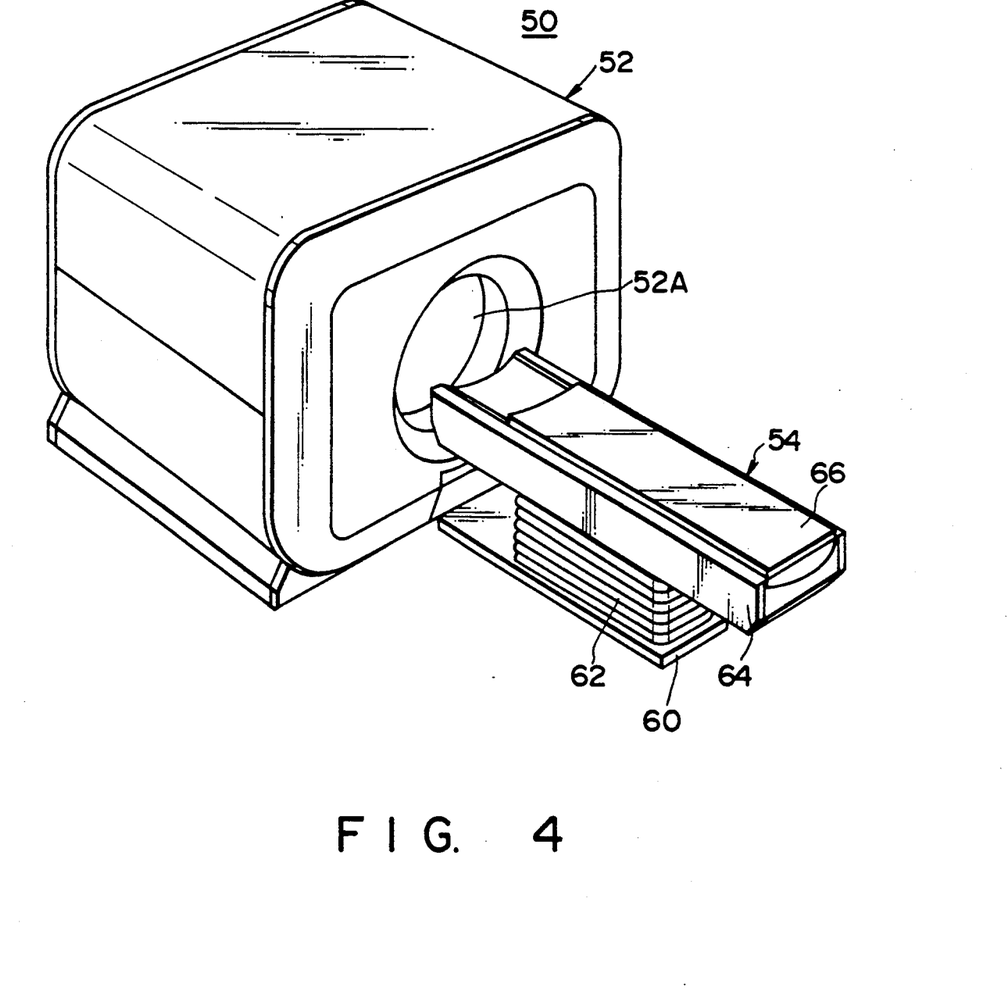
FIG. 4 is a perspective view of a magnetic resonance imaging apparatus including an apparatus of the present invention.

Prior to the description of the embodiments of the present invention, a magnetic resonance imaging (MRI) apparatus will now be described as a typical example of a medical apparatus in which the couch apparatus of the present invention is built in. As is shown in FIG. 4, MRI apparatus 50 comprises an apparatus body 52 for diagnosis and treatment, a couch apparatus 54 situated near the body 52 for moving a desired portion of a subject into a subject insertion hole 52A in apparatus body 52, and electric components (not shown). Within apparatus body 52, a static magnetic field generating device such as a super-conducting magnet, an inclined magnetic field coil, and a transmitting/receiving coil are assembled. A desired magnetic field is generated within the subject insertion hole 52A by the static magnetic field generating device, inclined magnetic field coil and transmitting/receiving coil. The generated magnetic field causes a magnetic resonance phenomenon to occur in the subject, which can be a living body.

The couch apparatus 54 comprises a lower base 60 fixed on the floor, an elevating mechanism 62 mounted on the lower base 60, an upper base 64 fixed on the upper part of the elevating mechanism 62, an elongated tabletop 66 situated slidably along the longitudinal axis of the upper base 64, and a tabletop sliding mechanism (not shown). The lower base 60, elevating mechanism 62 and upper base 64 constitute a base structure. The elevating mechanism 62 comprises an oil cylinder mechanism or an electric mechanism. Utilizing the cylinder mechanism, the elevating mechanism 62 raises and lowers the upper base 64. In FIG. 4, the inside of the elevating mechanism 62 is covered by a hood. The details of the upper base 64, tabletop 66, and the tabletop sliding mechanism (not shown) will be understood by reference to FIGS. 5 to 8.

Figure 5:
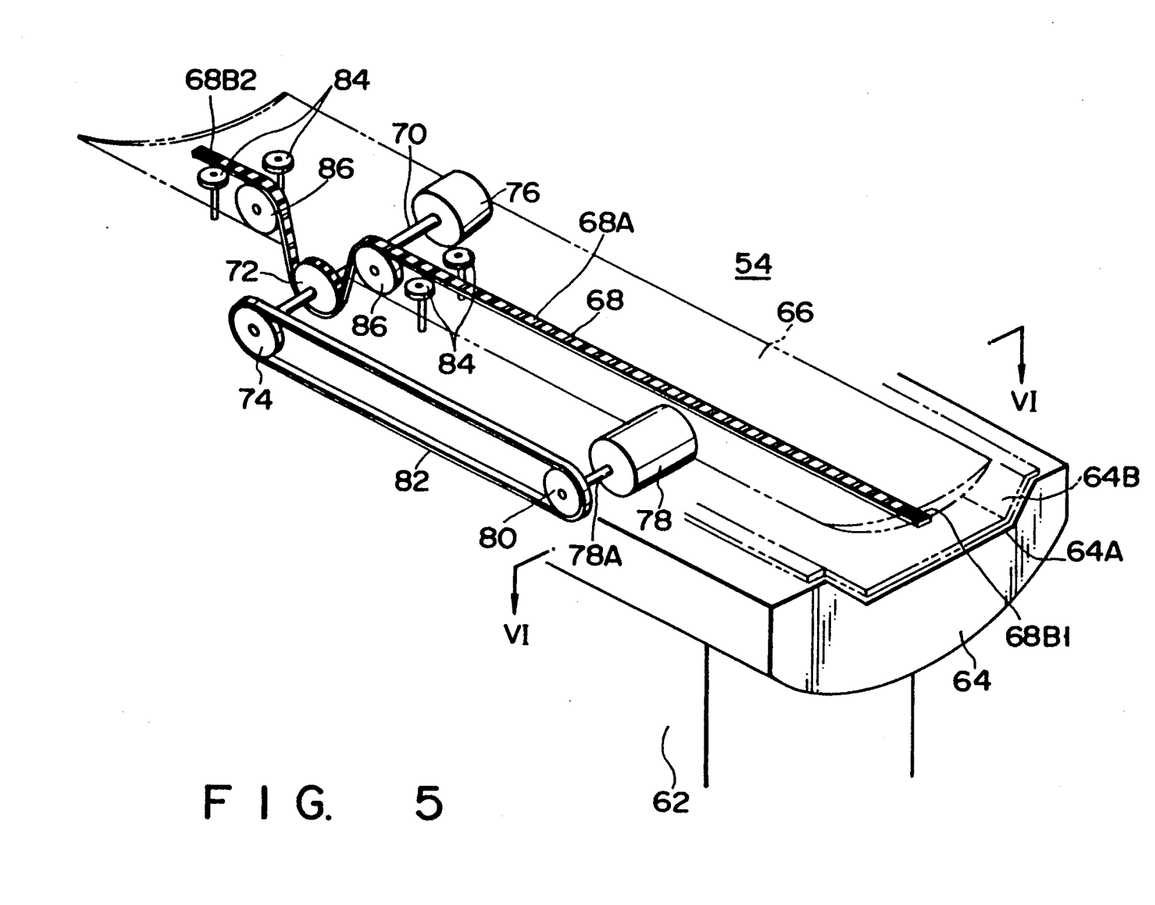
FIG. 5 is a partial cross-sectional view of a couch apparatus according to a first embodiment of the present invention, and, in particular, showing an upper base, a tabletop and a tabletop sliding mechanism of the couch apparatus.
Figure 6:
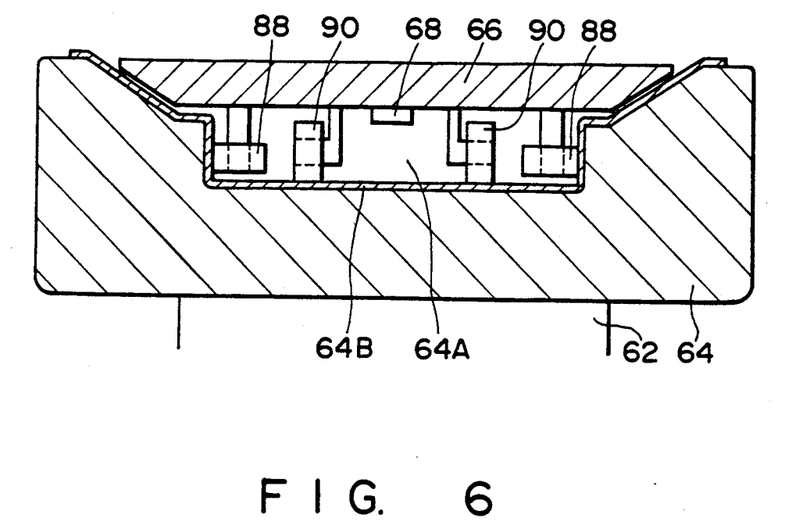
FIG. 6 is a cross-sectional view taken along line VI—VI in FIG. 5, showing an example of the tabletop guiding mechanism.

A first embodiment of the inventive couch apparatus 54 will now be described with reference to FIGS. 5 to 7. As shown in FIG. 5, a partial perspective view of the upper base 64, tabletop 66 and tabletop sliding mechanism of the couch apparatus, the upper base 64 has a recess 64A at its upper part. An axially middle portion of the upper base 64 is provided with a space (not shown) for receiving main components of the tabletop sliding mechanism such as a pulley 72 with gear teeth (described later). A patch plate 64B is formed over the recess 64A of the upper base 64.

The tabletop 66 is situated above the recess 64A of the upper base 64. The bottom surface of tabletop 66 is provided with a belt 68 with gear teeth 68A (a gear-toothed belt). A subject (not shown) is placed on the top surface of tabletop 66. The tabletop 66 is an elongated plate with a length and a width sufficient to support the subject, and it is desirably made of nonmagnetic material. The bottom of the tabletop 66 is provided with a tabletop guide mechanism as shown in FIG. 6 or FIG. 7. The details of the tabletop guide mechanism will be described later.

The gear-toothed belt 68 is a resilient elongated belt with a length greater than that of the tabletop 66, and it is desirably made of non-magnetic material. That side of the belt 68, on which gear teeth are formed, faces the bottom surface of the tabletop 66. One end of the gear-toothed belt 68 is fixed to one end of the tabletop 66, and the other end of the belt 68 is fixed to the other end of the tabletop 66. Belt 68 has a slack intermediate portion. Reference numerals 68B1 and 68B2 denote those portions of the gear-toothed belt 68 fixedly attached to opposite ends of tabletop 66.

A shaft 70 is rotatably situated in the aforementioned space of the upper base 64. The axial direction of the shaft 70 is aligned with the width direction of the upper base 64. The shaft 70 is coupled with gear-toothed pulley 72. An intermediate portion of belt 68 is passed under pulley 72. The teeth of pulley 72 are meshed with those of belt 68. One end of the shaft 70 is coupled to a first pulley 74, and the other end of the shaft 70 is coupled to an encoder 76. A stepping motor 78 is mounted on the upper base 64. A second pulley 80 is provided on a rotary shaft 78A of the stepping motor 78. The stepping motor 78 is rotated by a given angle in accordance with an applied pulse voltage. The rotation angle of the stepping motor 78 is proportional to the number of pulses of the applied pulse voltage, and the rotation speed of the stepping motor 78 is proportional to the frequency of the pulse voltage. Both the rotation angle and rotation speed can be controlled. An endless belt (timing belt) 82 is looped around the first pulley 74 and the second pulley 80.

The upper base 64 is provided with a belt guide mechanism for restricting the movement of the gear-toothed belt 68. The belt guide mechanism comprises a pair of guide rollers 84 for preventing the belt 68 from displacing in the width direction of the upper base 64, and guide pulleys 86 for smoothly moving the belt 68 along the longitudinal axis of the upper base 64. There are provided two guide rollers 84 and two guide pulleys 86. Two pairs of guide rollers 84 are shown in FIG. 5, with the rollers of each pair positioned, respectively, on both sides of belt 68. Guide pulleys 86 are provided, respectively, on both sides of the gear-toothed pulley 72. Pulleys 86 are separated along the longitudinal axis of belt 68.

The tabletop guide mechanism will now be described with reference to FIGS. 6 and 7. As is shown in FIG. 6, tabletop 66 is situated in the recess 64A of the upper base 64. The bottom surface of tabletop 66 is provided with a pair of guide rollers 88 for restricting width-directional movement of tabletop 66 (movement perpendicular to the longitudinal axis of tabletop 66), and a pair of guide rollers 90 for smoothing the axial movement of the tabletop 66 (movement parallel to the longitudinal axis of tabletop 66). A plurality of pairs of width-directional guide rollers 88 and axialdirectional guide rollers 90 are provided along the longitudinal axis of the tabletop 66 at predetermined intervals.

Figure 7:
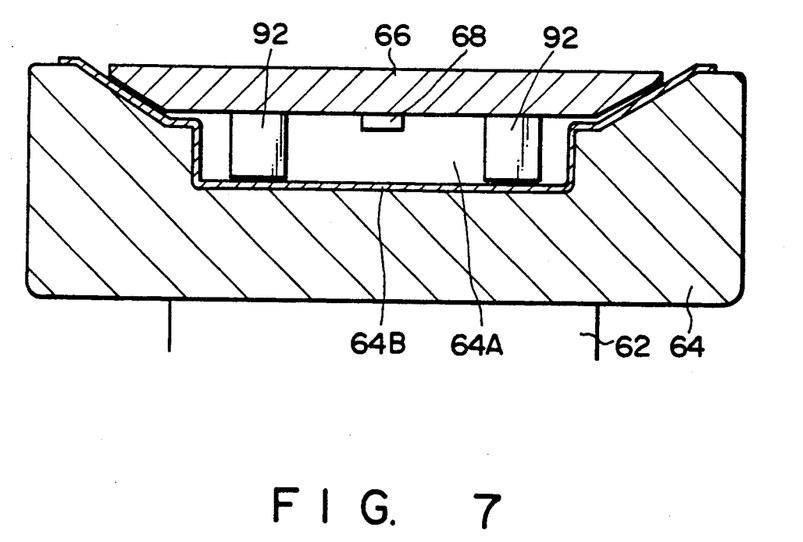
FIG. 7 is a cross-sectional view showing another example of a tabletop guiding mechanism useful with the FIG. 5 apparatus.

As shown in FIG. 7, tabletop 66 is situated in the recess 64A of the upper base 64. A pair of guide rails 92 are provided on the bottom surface of the tabletop 66.

The inventive couch apparatus having the above structure operates as follows. The subject is placed on the top of tabletop 66. A predetermined pulse voltage is applied to stepping motor 78. The stepping motor 78 rotates in accordance with the number of pulses and the frequency of the pulse voltage. The torque of the stepping motor 78 is transmitted to the pulley 74 through the pulley 80 and endless belt 82. In response, shaft 70 and drive pulley 72 are rotated by the torque exerted thereon by pulley 74. The drive pulley 72 rotates in one direction to run the toothed belt 68 in one direction. In accordance with the movement of the toothed belt 68, the tabletop 66 is moved while being supported by the tabletop guide mechanism provided in the recess 64A in the upper base 64. As is shown in FIG. 4, since the body 52 of the MRI apparatus is situated in a direction towards which the tabletop 66 can be moved, magnetic resonance imaging can be effected without causing any discomfort to the subject.

In the present invention, the stepping motor 78 is employed as a driving source. If power to the motor is cut off, the tabletop 66 can be easily moved manually. Any type of motor, other than the stepping motor 78, can be employed as a driving source.

As has been described above, in the couch apparatus 54 of the first embodiment, the driving mechanism cannot be seen from the outside. Therefore, no discomfort is caused to the subject, and good external appearance of the couch apparatus is maintained. In addition, by virtue of the simple structure, the manufacturing cost can be reduced.

Figure 8:
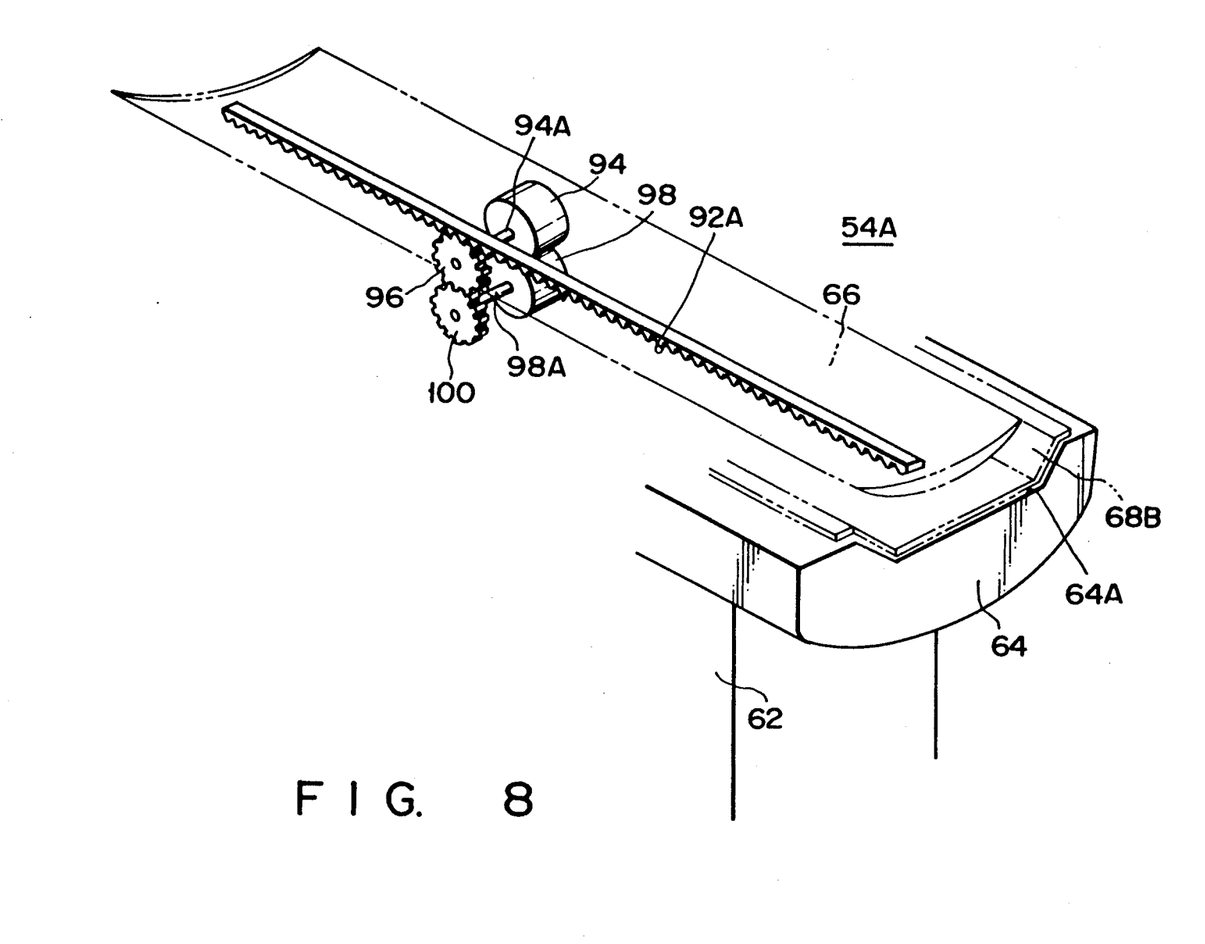
FIG. 8 is a perspective view showing a portion of a couch apparatus according to a second embodiment of the invention, in particular, the upper base, tabletop and tabletop sliding mechanism of the couch apparatus.

A couch apparatus 54A for medical use according to a second embodiment of the present invention will now be described with reference to FIG. 8. In FIG. 8, the common structural elements already shown in FIGS. 5, 6 and 7 are denoted by the same reference numerals as in FIGS. 5-7. The couch apparatus 54A according to the second embodiment shown in FIG. 8 comprises the tabletop guide mechanism shown in FIG. 6 or FIG. 7. Specifically, FIG. 8 is a perspective view of a portion of the upper base 64, tabletop 66 and tabletop sliding mechanism of the couch apparatus 54A according to the second embodiment. As shown in FIG. 8, the tabletop 66 is situated in the recess 64A of the upper base 64. A rack gear 92A is provided on the bottom surface of the tabletop 66, in place of belt 68 of FIG. 5. The rack gear 92A is desirably made of non-magnetic material. That side of the rack gear 92A on which teeth are formed, faces the bottom surface of the tabletop 66.

A stepping motor 94 is mounted in a space formed in a substantially middle portion of the upper base 64. A pinion gear 96 is coupled to a rotary shaft 94A of the stepping motor 94. The pinion gear 96 is meshed with the rack gear 92A An encoder 98 is also provided in the space formed in the middle portion of the upper base 64. A gear 100 is coupled to a rotary shaft 98A of the encoder 98. The gear 100 is meshed with the pinion gear 96.

The couch apparatus 54A of FIG. 8 operates like the couch apparatus 54 of FIG. 5, except that motor 94 causes gear 92A to translate table 66 in FIG. 8, whereas motor 78 causes belt 68 to translate table 66 in FIG. 5.

Figure 9:
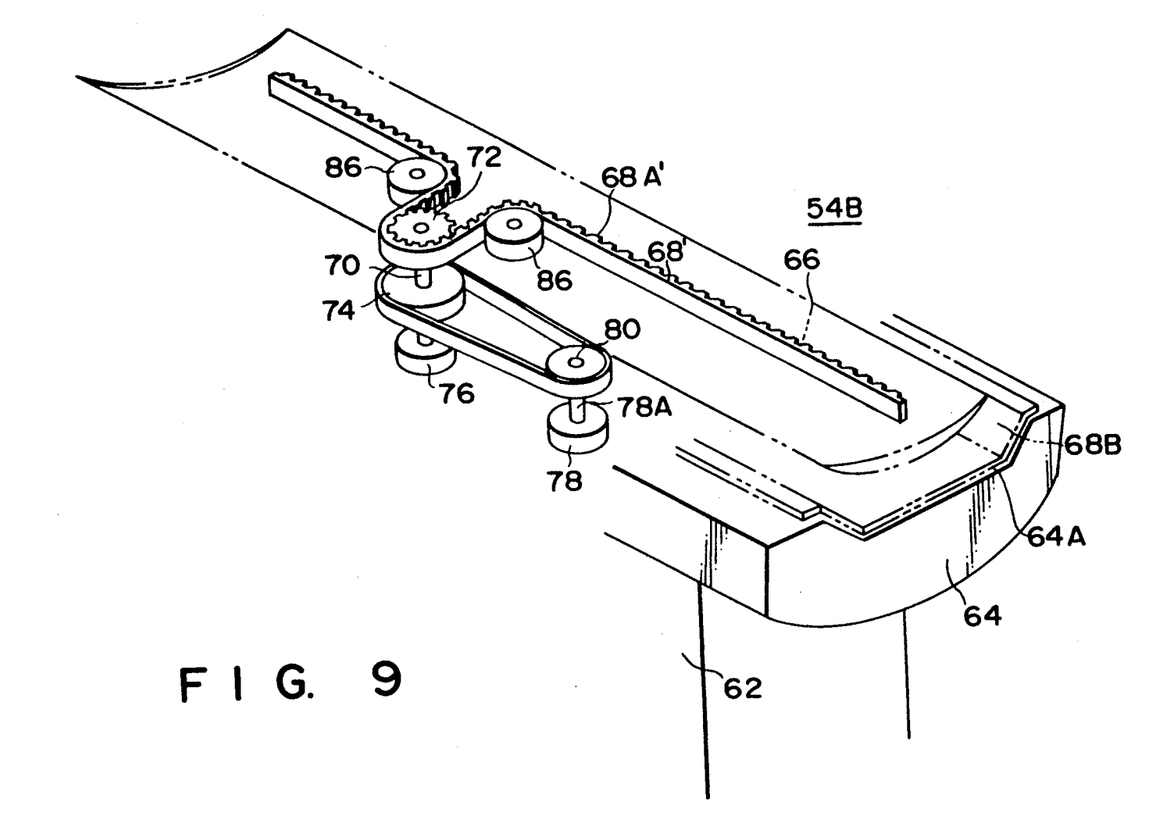
FIG. 9 is a perspective view showing a portion of a couch apparatus according to a third embodiment of the invention, in particular, the upper base, tabletop and tabletop sliding mechanism of the couch apparatus.

A couch apparatus 54B according to a third embodiment of the present invention will now be described with reference to FIG. 9. In FIG. 9, the common structural elements already shown in FIGS. 5, 6 and 7 are denoted by like reference numerals. The couch apparatus 54B according to the third embodiment shown in FIG. 9 has a belt 68' with gear teeth 68A (gear-toothed belt). That side of the belt 68', on which gear teeth 68A' are formed, face the side direction of the tabletop 66.

Figure 10:
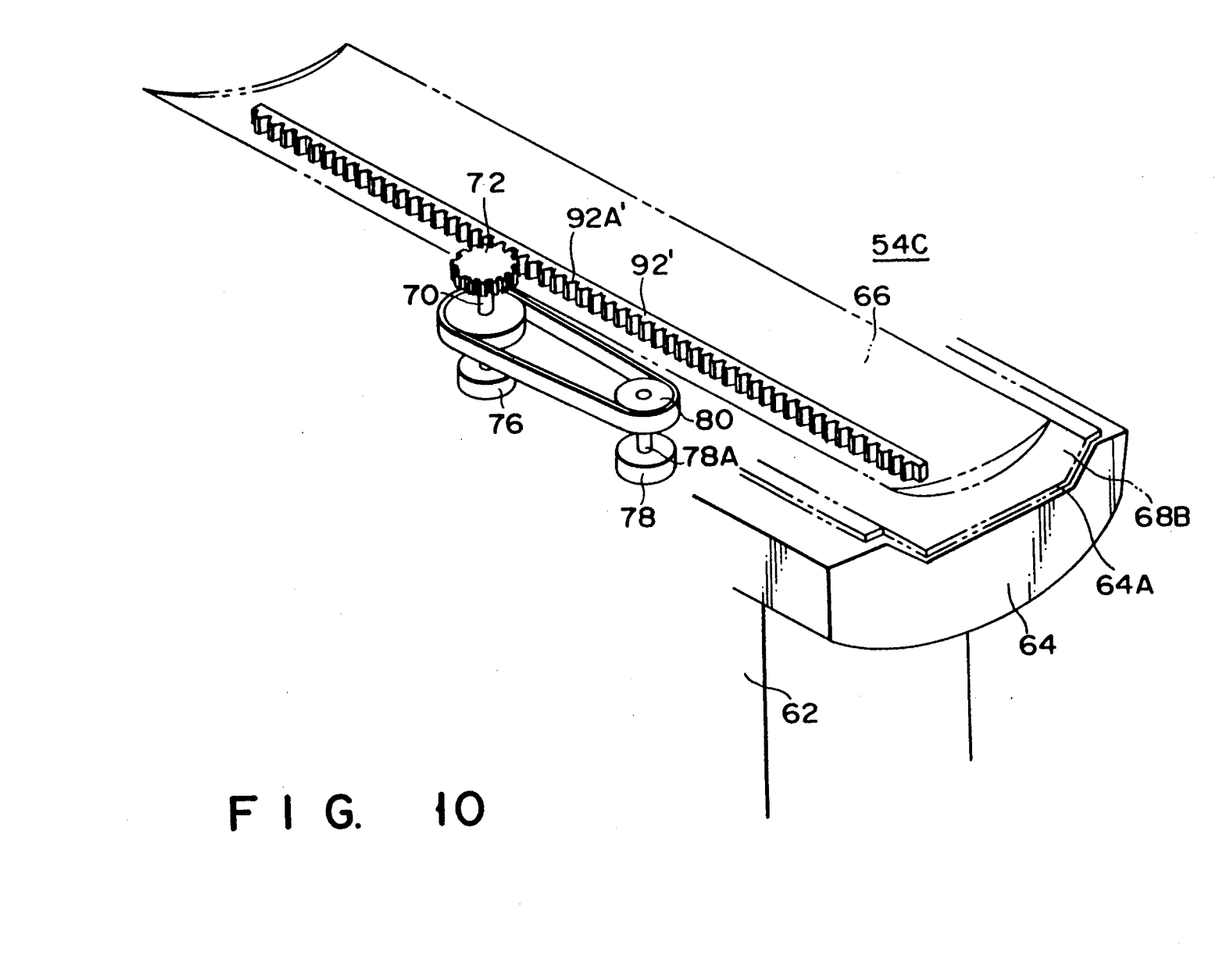
FIG. 10 is a perspective view showing a portion of a couch apparatus according to a fourth embodiment of the invention, in particular, the upper base, tabletop and tabletop sliding mechanism of the couch apparatus.

A couch apparatus 54C according to a fourth embodiment of the present invention will now be described with reference to FIG. 10. In FIG. 10, the common structural elements already shown in FIGS. 5 and 8 are denoted by like reference numerals. The couch apparatus 54C according to the fourth embodiment shown in FIG. 10 has a rack gear 92'. That side 92A' of the rack gear 92', on which gear teeth are formed, faces the side direction of the tabletop 66.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A couch apparatus for medical use, comprising:
   a tabletop having a first end portion and a second end portion, wherein the second end portion is separated from the first end portion along a longitudinal axis;
   a base structure on which the tabletop is slidably mounted;
   a belt means having a first end fixed to the first end portion of the tabletop and a second end fixed to the second end portion of the tabletop, wherein the belt means extends along the longitudinal axis and has a slack intermediate portion between the first end and the second end;
   at least one pair of belt guide members attached to the base structure in positions for restricting motion of the belt means in directions perpendicular to the longitudinal axis as a drive pulley means translates the belt means;
   a drive pulley means mounted on the base structure in engagement with said intermediate portion of the belt means; and
   a driving means mounted on the base structure in engagement with the drive pulley means, for rotating the drive pulley means, thereby causing the drive pulley means to translate the belt means along the longitudinal axis relative to the base structure as said drive pulley means rotates.

2. The apparatus according to claim 1, wherein said base structure comprises:
   a fixedly mounted lower base;
   an elevating mechanism having a lower portion fixedly attached to the lower base; and
   an upper base fixedly attached to an upper part of the elevating mechanism, wherein said tabletop is slidably mounted to said upper base.

3. The apparatus according to claim 1, wherein the drive pulley means has teeth, and wherein said belt means has gear teeth dimensioned to mate with the teeth of the drive pulley means.

4. The apparatus according to claim 1, also including:

at least one guide pulley mounted to the base structure in engagement with the belt means in a position for smoothing longitudinal movement of the belt means.

5. The apparatus according to claim 1, also including a tabletop guide mechanism mounted to at least one of the tabletop and the base structure in a position for guiding the belt means as said drive pulley means translates the belt means, said tabletop guide mechanism including at least one width-directional guide roller mounted to the tabletop in a position for restricting displacement of the tabletop in a direction perpendicular to the longitudinal axis.

6. The apparatus according to claim 5, wherein said tabletop guide mechanism comprises at least one elongated guide rail fixed to a bottom surface of the tabletop.

7. The apparatus according to claim 1, wherein at least one of the tabletop and the belt means is made of a non-magnetic material.

8. The apparatus according to claim 1, wherein said driving means includes a stepping motor mounted to the base structure.

9. The apparatus according to claim 1, wherein said driving means comprises:
  a motor having a shaft;
  at least one motor pulley mounted on the shaft of the motor; and
  an endless belt looped around both the at least one motor pulley and said drive pulley means.

10. The apparatus according to claim 1, wherein said drive pulley means includes an encoder for detecting rotational orientation of the drive pulley means.

* * * * *